US005649447A

United States Patent [19]
Van Avery

[11] Patent Number: 5,649,447
[45] Date of Patent: Jul. 22, 1997

[54] NON DESTRUCTIVE PAINT AND BONDING ADHESION PREDICTION METER (APM) FOR METAL SURFACES

[75] Inventor: James C. Van Avery, Renton, Wash.

[73] Assignee: The Boeing Company, Seattle, Wash.

[21] Appl. No.: 687,275

[22] Filed: Jul. 25, 1996

[51] Int. Cl.⁶ ................................................. G01N 19/04
[52] U.S. Cl. ........................................... 73/150 A; 73/827
[58] Field of Search ........................... 73/150 A, 159, 73/827

[56] References Cited

U.S. PATENT DOCUMENTS

| 2,473,517 | 6/1949 | Freedman | 73/150 A |
| 3,019,644 | 2/1962 | Mancini | 73/150 A |
| 3,524,345 | 8/1970 | Isaacson | 73/150 A |
| 4,188,824 | 2/1980 | McCarthy | 73/150 A |
| 4,893,503 | 1/1990 | Kimura et al. | 73/150 A |
| 4,893,513 | 1/1990 | Schroeder et al. | 73/150 A |

FOREIGN PATENT DOCUMENTS

| 0027636 | 3/1981 | Japan | 73/150 A |
| 0044834 | 3/1982 | Japan | 73/150 A |
| 261029 | 11/1987 | Japan | 73/150 A |
| 0154136 | 6/1990 | Japan | 73/150 A |
| 1019297 | 5/1983 | U.S.S.R. | 73/150 A |

*Primary Examiner*—Diego F. F. Gutierrez
*Attorney, Agent, or Firm*—Conrad O. Gardner

[57] ABSTRACT

A method of predicting the adhesion of a metal surface for painting or bonding comprising pressing an elastomer pad against the surface with a known force for a certain minimum time, measuring the force required to pull the pad away from the surface, and comparing that force with an empirically derived standard.

3 Claims, 2 Drawing Sheets

NON DESTRUCTIVE PAINT AND BONDING ADHESION PREDICTION METER (APM) FOR METAL SURFACES

BACKGROUND OF THE INVENTION

1. Field of the Invention

This invention relates to an instrument for use in metal surface preparation and more specifically for an apparatus and method for determining metal surface adhesion quality.

2. Background Information

Exemplary of the prior art patent literature on prediction of adhesion quality is U.S. Pat. No. 4,188,824 (Edward P. McCarthy) which discloses a method for predicting the adherence propensity of a metal substrate by applying a piece of clear tape to the surface, removing it, and comparing the amount of "soil" on the tape with a set of standards.

Prior methods of paint adhesion prediction have required destructive testing of a sample after the fact. Accordingly, it is an object of the present invention to provide means for allowing quantification and predictions of adhesiveness beyond those that can be tested by destructive methods.

SUMMARY OF THE INVENTION

The present invention provides a portable, inexpensive, and production-usable surface preparation meter for pre-painted aluminum. Pressing a synthetic elastomer pad to the metal surface enables a force meter to indicate if the conversion coating, such as Alodine (a mild acid), which is a registered trademark under the product trade name: Alodine 1000 Liquid; of Parker & Amchem, 32100 Stephinson Highway, Madison Heights, Mich. 48071, or anodize, is sufficient for the required adhesion. This is accomplished by comparing relative readings from the unit under test with known good readings acquired empirically.

BRIEF DESCRIPTION OF THE DRAWING(S)

DESCRIPTION OF THE PREFERRED EMBODIMENT(S)

Introduction

The effect of surface roughness on an aluminum oxide surface is critical and intimately related to paint bonding. It is an object of this invention to provide an instrument that can quickly measure the oxide surface for sufficient roughness prior to painting. This includes conversion coating processes such as Alodine or anodize.

Recent discoveries show that certain elastomers exhibit an adhesion response directly related to microscopic variations in roughness and cleanliness. The present apparatus predicts paint and bonding adhesion to metals. It is suspected that the majority of intermittent adhesion problems in industry are caused by variables in surface preparation.

The adhesion quality of a prepared aluminum surface is impossible to visibly detect. There is presently no objective field test method to inspect for proper surface conditions after applying a conversion coating such as Alodine. As a consequence, a nondestructive method that can indicate surface adhesion quality would be very desirable and is believed provided by the hereinafter described method and apparatus.

Adhesion Prediction Meter Description

Figure 1:
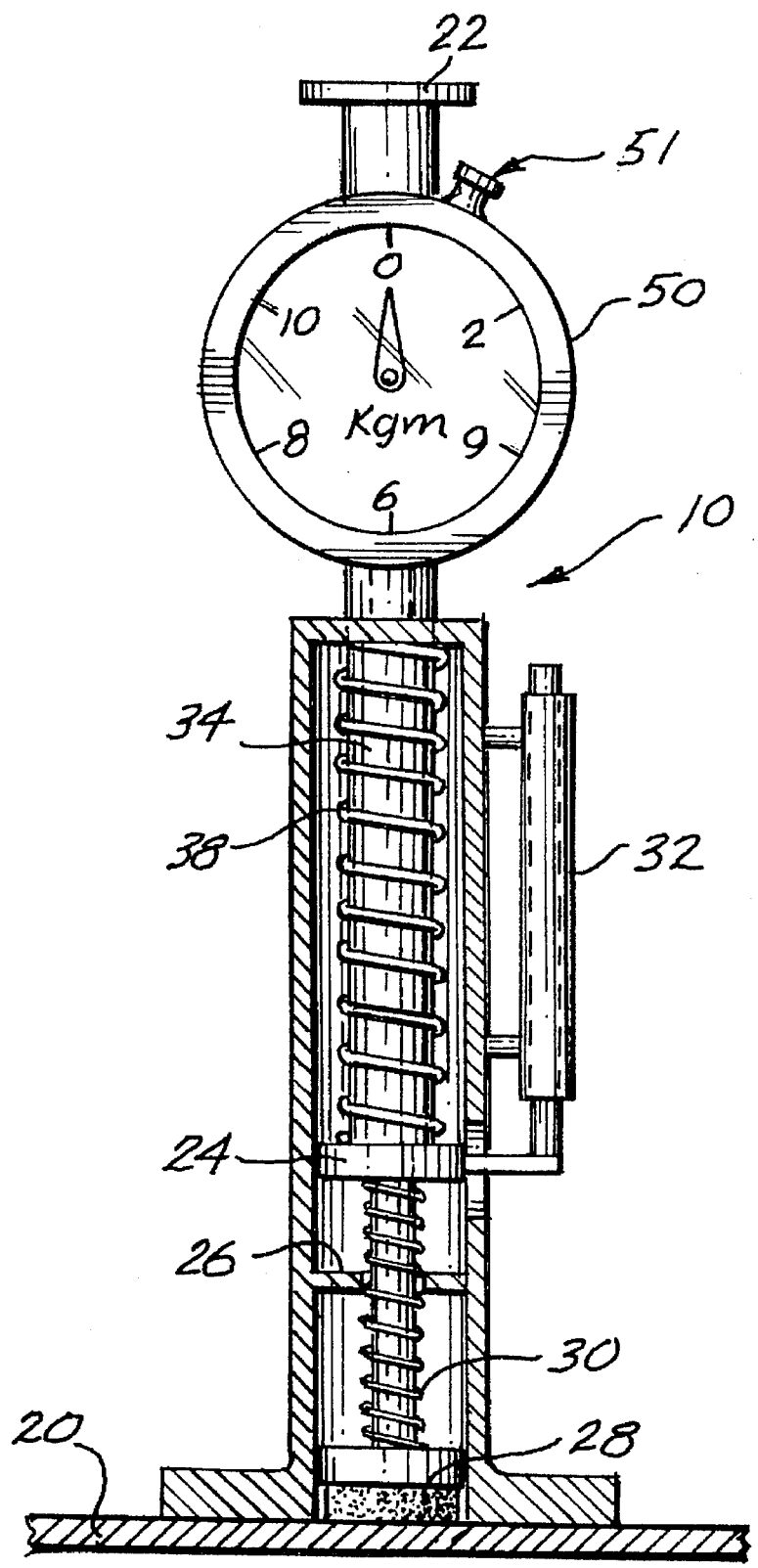
FIG. 1 is a front view of the present adhesion prediction apparatus.

The Adhesion Prediction Meter (APM) 10 is shown in FIG. 1. A reading is taken by placing the instrument on the surface 20 to be tested and pushing down on handle 22 until the upper plunger pressure foot 24 contacts the stop 26 for a minimum of 3 seconds. This applies a constant force to elastomer adhesive pad 28 by way of the compression spring 30 for constant force applied to elastomer adhesive pad 28. Releasing pressure from handle 22 allows the upper plunger lever to come in contact with shock absorber piston 32 while force gauge connection cable 34 becomes taut. Next, tension spring 38 and shock absorber 32 combination applies a steady pull rate to elastomer adhesive pad 28 until it releases from metal surface 20 under test. Meanwhile, the coil spring inside force gauge 50 registers the pull force and captures the release-force reading on the meter. Relative readings are indicated; higher readings are proportional to increased surface roughness.

Instrument 10 is made up of three basic parts:

1. Removable elastomer pad 28.

A proprietary synthetic elastomer material has been specially designed that appears to react like miniature Velcro (which is a registered trademark of Velcro Fastening Systems, 406 Brown Avenue, Manchester, N.H. 03108). The material is very sensitive to microscopic changes in the porosity of the oxide surface. It is assumed that when the elastomer is pushed hard enough on the oxide surface, small portions of it are forced into the microscopic pores and cracks of the surface, or it encompasses oxide fibers causing the bond strength.

2. Push-pull spring and shock absorber mechanism.

Two springs 30 and 38 are used to control the pushing force and the pulling rate. Pressure is applied to handle 22 by the operator until upper plunger pressure foot 24 reaches stop 26. Compression spring 30 presses elastomer pad 28 to metal surface 20 with a set repeatable force. This force is held for a minimum of 3 seconds. The tension spring 38 pulls pad 28 from the surface 20 when the plunger is released. The pull rate is controlled by an adjustable-rate hydraulic shock absorber. Full travel is ½ inch and takes approximately 5 seconds.

3. Pull force indicator

As tension spring 38 and connection cable 34 combination slowly applies more pull force to adhesive rubber pad 28, force meter readings 50 increase until pad 28 breaks away from metal surface 20. Meter 50 holds the breakaway force reading for operator observation until meter reset button 51 is depressed. Increased force readings are proportional to surface roughness. Indications have shown to be repeatable. Slight roughness variations created by time differences in the Alodine process are detectable. Empirical calibration of the readings is required when comparing the force readings to predict specific paint type adhesive due to molecular bonding differences.

Experimental Results

The APM was tested on different aluminum alloys and conversion coatings to get an overview of what it could detect. It was found that variations in the processes used in conversion coating metals gave observable differences. Conversion coatings such as Alodine and anodize were examined. These processes have always been known to be critical to parameters, such as time applied, solution concentrations, and agitation during process.

Figure 2:
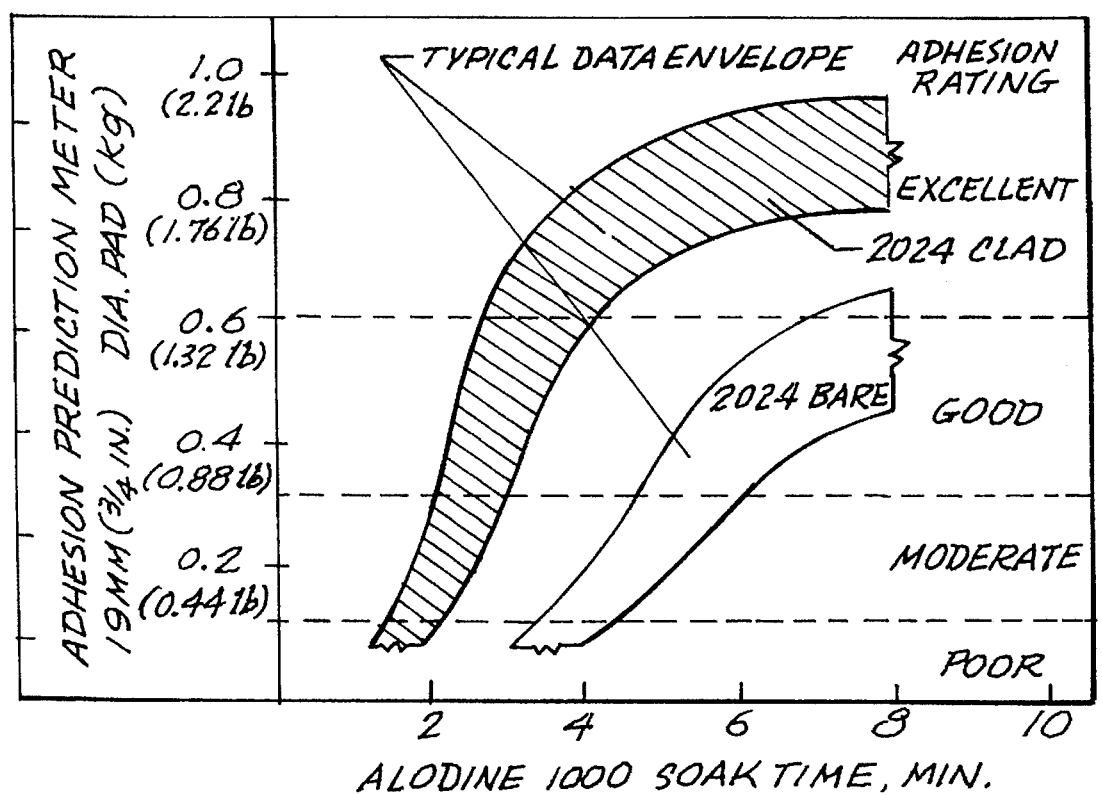
FIG. 2 is a graph depicting APM reading variations to Alodine soak time and an emperical paint adhesion test on aluminum.

The time factor of application is an easy variable to control; therefore, this was the method chosen to vary surface roughness for all testing (see FIG. 2). Two alloys of aluminum were examined, 2024 bare and clad. The major difference between these two alloys is the concentration of aluminum. Bare is approximately 95.7% pure and clad is approximately 99.3% pure. It is known that oxidation using acidic conversion coatings such as chromic acid Alodine will vary with different alloys. This was easily shown using the present APM. Bond strength will increase for increases in application time. Clad aluminum gives higher bond readings than bare for the same amount of process time.

Elastomer Pad 28

Material that has been used for elastomer pad 28 was purchased from:
1. Chromerics, Inc., 77 Dragon Court, Woburn, Mass. 01888-4010.
   Specify:
   1. CHO-SEAL 1285 Silicon
   2. CHO-SEAL 1287 fluorosilicon
2. Stockwell Rubber Co., 4749 Tolbut Street, Philadelphia, Pa. 19136
   Specify:
   1. SCF444 Silicon The material that was found to be the most forgiving to the metal surface tested, as far as leaving traces of silicon deposits, was the Chromerics CHO-SEAL 1287 fluorosilicon. After testing, the metallic surface must be lightly wiped with a soft cotton lint free cloth preferably soaked with acetone.

Initial Preparation of the Elastomer Surface

The purchased elastomer materials must be processed as follows:

The miniature conductive metallic balls impregnated in the elastomer must be removed from the surface before it will adhere to metallic surfaces.

The following steps are required to remove the metallic spheres:
1. Cut the elastomer into the desired size, 0.75 inch diameter.
2. Adhere to an application stud with silicon adhesive.
3. Lightly hand rub the elastomer surface on 400 grit sandpaper after the surface has been completely saturated with a mild liquid soap (Klenz lotion, hand soap, from Calgon Vestal Laboratories, St. Louis, Mo. 63133) and some water to dilute the soap to a workable solution. The elastomer surface should be rubbed and rinsed with water until the silver color from the embedded spheres disappears. Elastomer should have a uniform blue color after the spheres have been removed.

Elastomer Test Pad 28 Cleaning

The pad will pick up dirt and contamination from the surfaces under test during use. The pad can be cleaned with the same soap used in the initial preparation. Rubbing with the finger and ample amounts of soap will easily clean the surface. All soap must be rinsed off the pad before use. There should be a slight friction to the touch when all the soap is removed. Light sanding, as described in the initial preparation, will keep the surface active indefinitely.

Conclusions

The herein before described APM is very efficient in giving a go-no/go indication in specific areas or monitoring problem areas over time. It is very effective during laboratory testing in arriving at the best conditions for improved process control.

Predictive adhesion testing using the present APM takes into consideration the prepared surface conditions concerning roughness and organic cleanliness. It gives repeatable and objective results and has the ability to take the guesswork out of surface inspection prior to painting or bonding.

What is claimed is:

1. A method for determining adhesion characteristics of a metal surface comprising the steps of:

disposing an adhesive elastomer pad on said metal surface, said pad being sensitive to microscopic changes in the porosity of said metal surface;

applying a constant force to said adhesive elastomer pad for a predetermined period of time;

applying a steady pull rate to said adhesive elastomer pad until said adhesive elastomer pad releases from said metal surface;

determining the release force when said adhesive elastomer pad breaks away from said metal surface, said release force being representative of the surface roughness of said metal surface; and determining the adhesion characteristics of said metal surface by comparing the determined release force with an empirically derived standard.

2. The method according to claim 1 wherein said predetermined period of time exceeds about 3 seconds.

3. In combination in an apparatus for determining adhesion characteristics of a metal surface by comparing a breakaway force with an empirically derived standard, said metal surface being an oxide metal surface, a removable elastomer pad sensitive to microscopic changes in the porosity of said oxide metal surface;

said removable elastomer pad being disposed on said metal surface and being applied a pushing force and a pulling rate;

a push-pull spring and shock absorber mechanism for controlling the pushing force and pulling rate applied to said removable elastomer pad; and a readout device for determining the breakaway force when said removable elastomer pad breaks away from said metal surface during application of the pulling rate.

* * * * *